(12) United States Patent
Alberto

(10) Patent No.: US 6,780,300 B1
(45) Date of Patent: Aug. 24, 2004

(54) DEVICE FOR ANALYZING SAMPLES BY MULTI-CAPILLARY ELECTROPHORESIS WITH SOLID/SOLID TEMPERATURE REGULATION

(75) Inventor: Fei Alberto, Firenze (IT)

(73) Assignee: Sebia (FR)

(*) Notice: Subject to any disclaimer, the term of this patent is extended or adjusted under 35 U.S.C. 154(b) by 59 days.

(21) Appl. No.: 09/628,453

(22) Filed: Jul. 31, 2000

(30) Foreign Application Priority Data

Apr. 25, 2000 (FR) .............................................. 00 05255

(51) Int. Cl.$^7$ .............................. C02F 1/40; C02F 11/00; C25B 11/00; C25B 13/00; C25B 9/00
(52) U.S. Cl. .................................................................. 204/601
(58) Field of Search ........................................ 204/601

(56) References Cited

U.S. PATENT DOCUMENTS

| | | | |
|---|---|---|---|
| 4,985,129 A | * 1/1991 | Burd | 204/603 |
| 5,045,172 A | 9/1991 | Guzman | 204/299 R |
| 5,061,361 A | 10/1991 | Gordon | 204/299 R |
| 5,066,382 A | * 11/1991 | Weinberger et al. | 204/451 |
| 5,085,757 A | * 2/1992 | Karger et al. | 204/603 |
| 5,164,064 A | * 11/1992 | Dill et al. | 204/601 |
| 5,171,531 A | * 12/1992 | Christianson et al. | 422/102 |
| 5,198,091 A | * 3/1993 | Burolla et al. | 204/601 |
| 5,356,525 A | * 10/1994 | Goodale et al. | 204/602 |
| 5,413,686 A | 5/1995 | Klein et al. | 204/299 R |
| 5,458,761 A | 10/1995 | Kamahori et al. | 294/299 |
| 5,753,094 A | * 5/1998 | Alter et al. | 204/451 |
| 5,790,727 A | * 8/1998 | Dhadwal et al. | 385/38 |
| 5,898,493 A | 4/1999 | Jankowiak et al. | 356/318 |
| 5,900,132 A | * 5/1999 | Keenan et al. | 204/603 |
| 5,908,552 A | * 6/1999 | Dittmann et al. | 210/198.2 |
| 5,964,998 A | * 10/1999 | Kambara | 204/452 |
| 5,968,331 A | * 10/1999 | Kambara et al. | 204/450 |
| 6,001,230 A | * 12/1999 | Burolla | 204/453 |
| 6,017,765 A | * 1/2000 | Yamada et al. | 204/602 |
| 6,027,627 A | 2/2000 | Li et al. | 204/603 |
| 6,103,081 A | * 8/2000 | Morris et al. | 204/451 |
| 6,120,667 A | * 9/2000 | Hayashizaki et al. | 204/603 |
| 6,156,178 A | * 12/2000 | Mansfield et al. | 204/450 |
| 6,258,238 B1 | * 7/2001 | Buttner et al. | 204/603 |
| 6,375,819 B1 | * 4/2002 | Li et al. | 204/455 |
| 6,428,670 B1 | * 8/2002 | Hayashizaki et al. | 204/601 |

FOREIGN PATENT DOCUMENTS

| | | |
|---|---|---|
| EP | 0 386 925 | 2/1990 |
| EP | 0854 362 A2 | 7/1998 |

OTHER PUBLICATIONS

"Capillary Array Electrophoresis," *Analytical Chemistry News & Features*, Jan. 1, 1999.

Lukkari, et al.: "Home–Made Temperature–Control Unit for the Waters Quanta 4000 Capillary Electrophoresis System," *HRC Journal of High Resolution Chromography* 17 (1984) Sep., No. 3, Heidelberg, DE.

* cited by examiner

*Primary Examiner*—Mark L. Bell
*Assistant Examiner*—Jennine M. Brown
(74) *Attorney, Agent, or Firm*—Lerner, David, Littenberg, Krumholz & Mentlik, LLP

(57) ABSTRACT

A device for analyzing samples by electrophoresis comprises a plurality of capillaries, receiver means comprising a multiplicity of independent units each made of a material that is thermally conductive and electrically insulating, and designed to be closely enclosed over the central portion of a capillary, and temperature regulator means comprising at least one Peltier unit for exchanging heat with the units via a solid/solid exchange so as to regulate the temperature of the capillaries via said units.

27 Claims, 5 Drawing Sheets

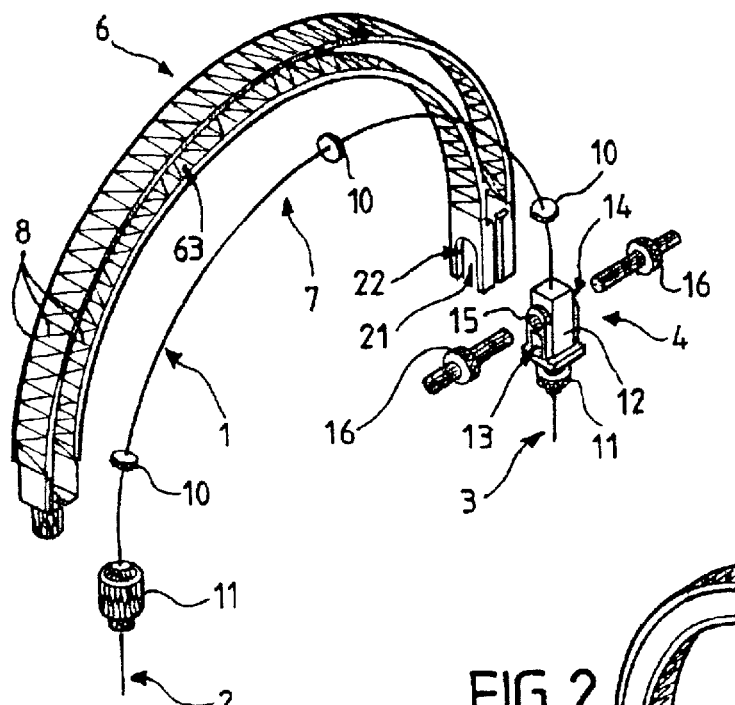
FIG_1
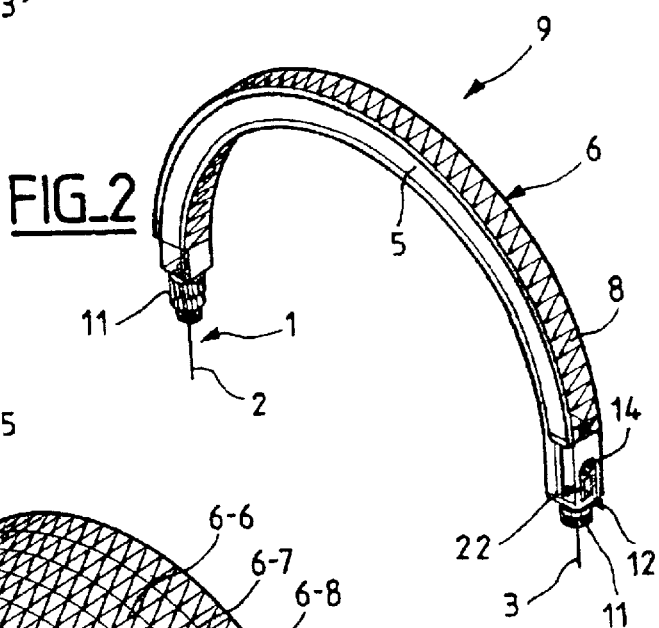
FIG_2
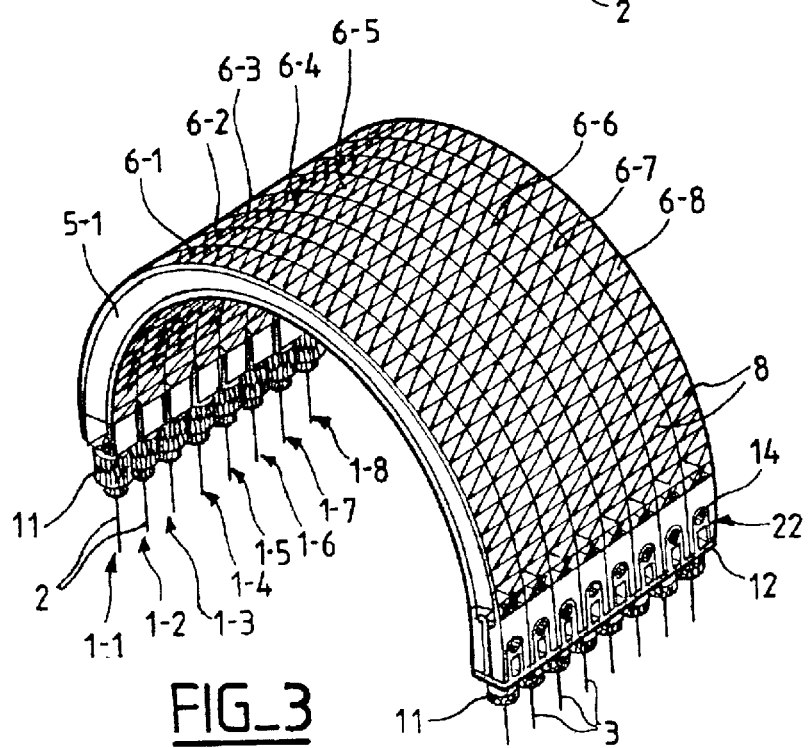
FIG_3

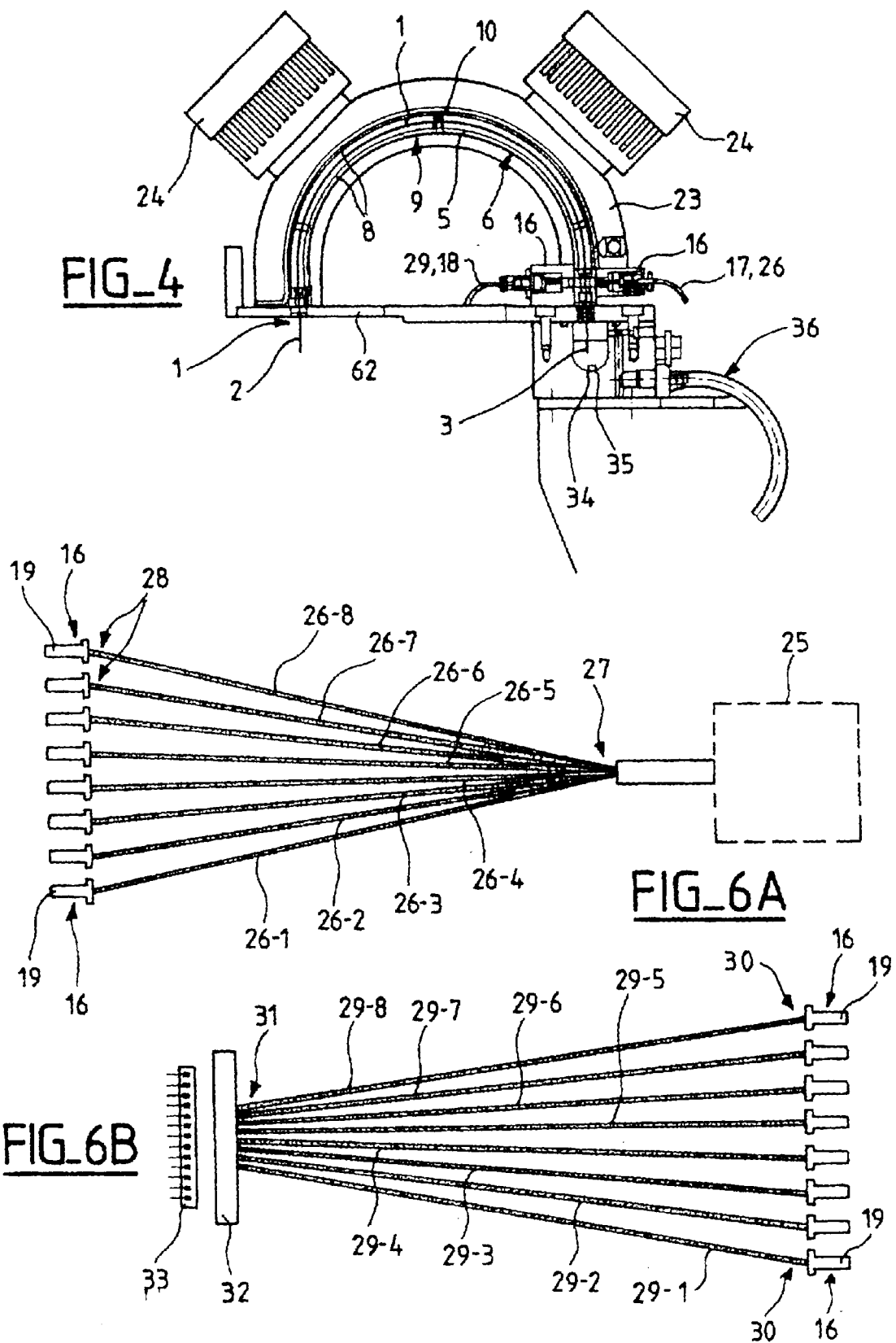

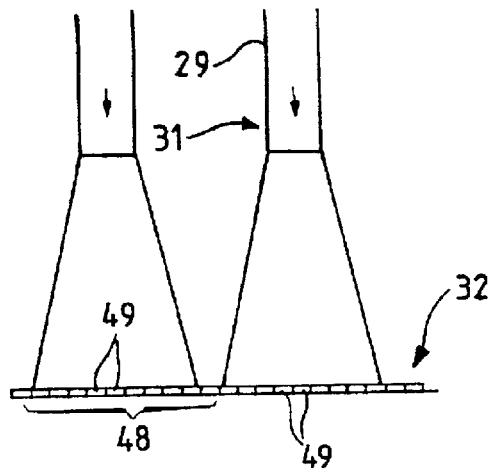
FIG_7
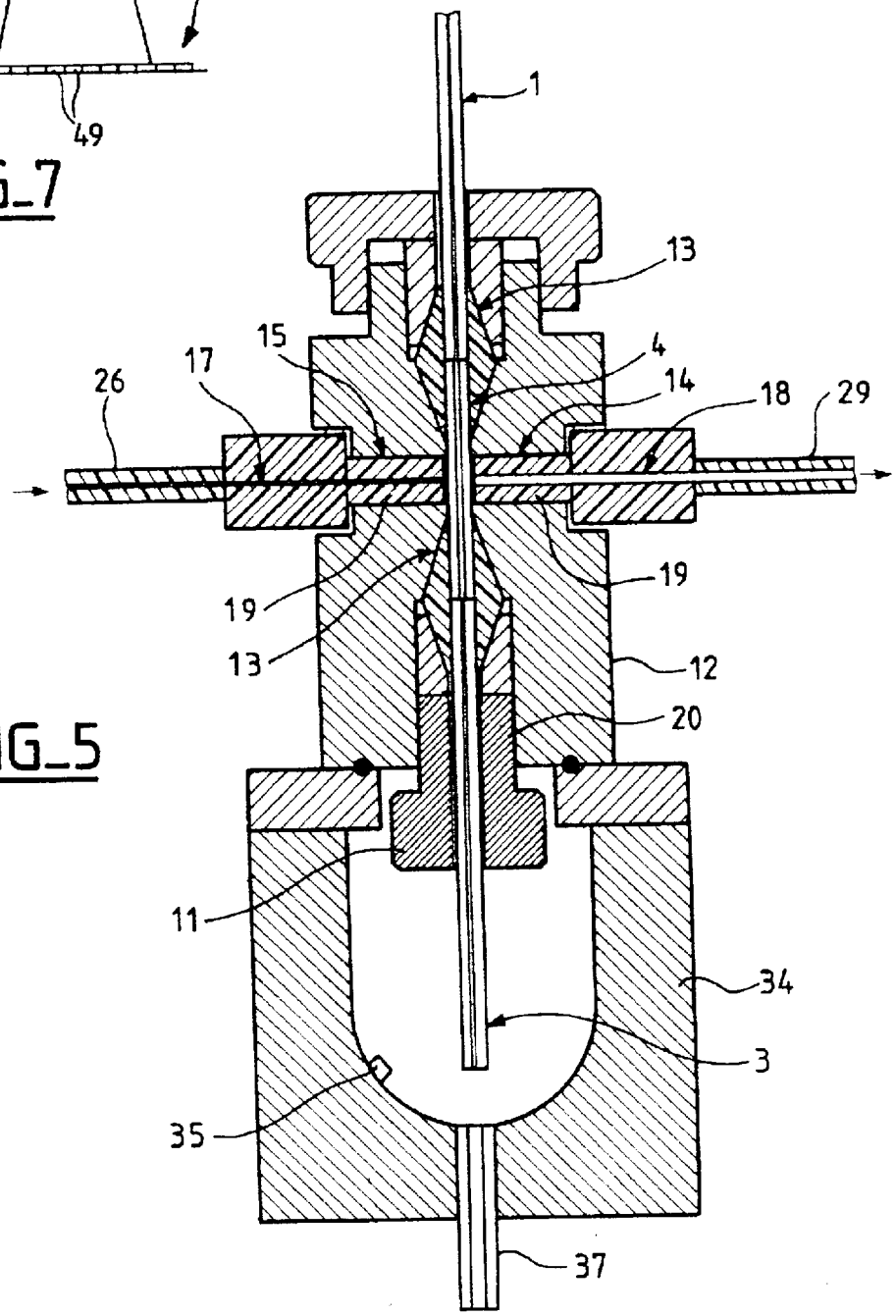
FIG_5

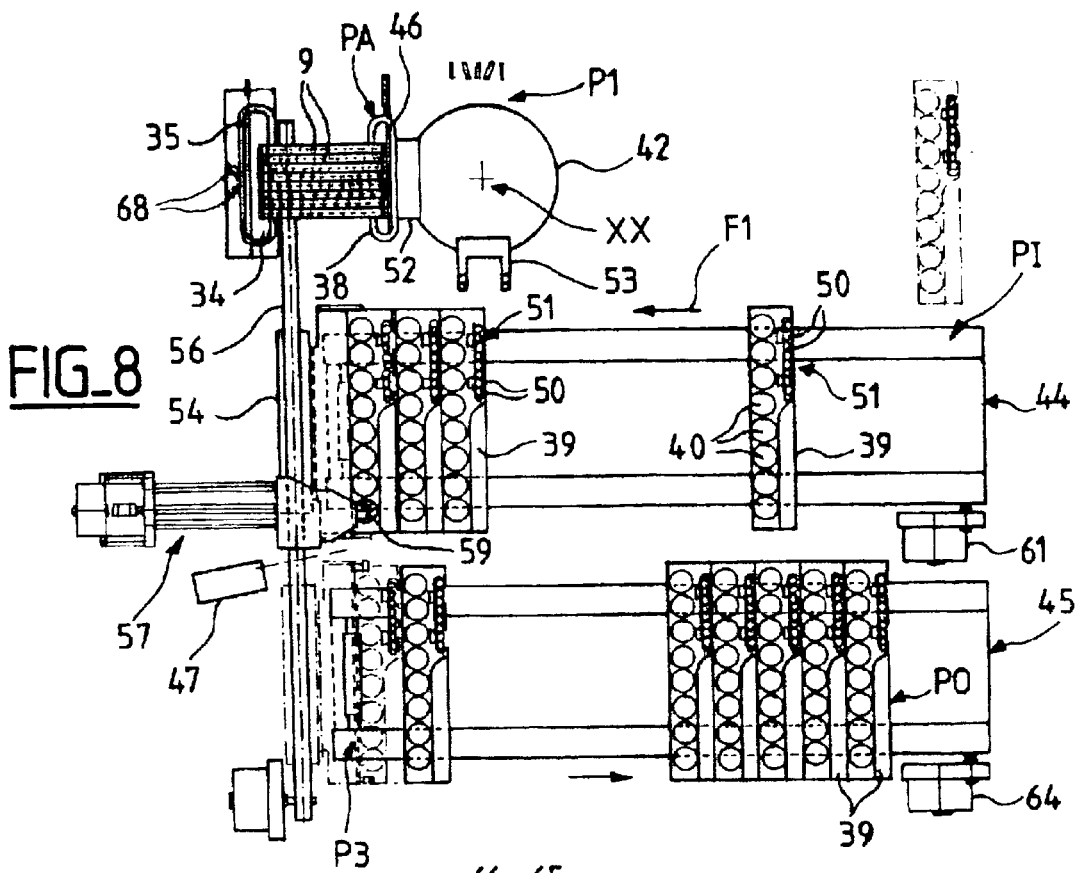
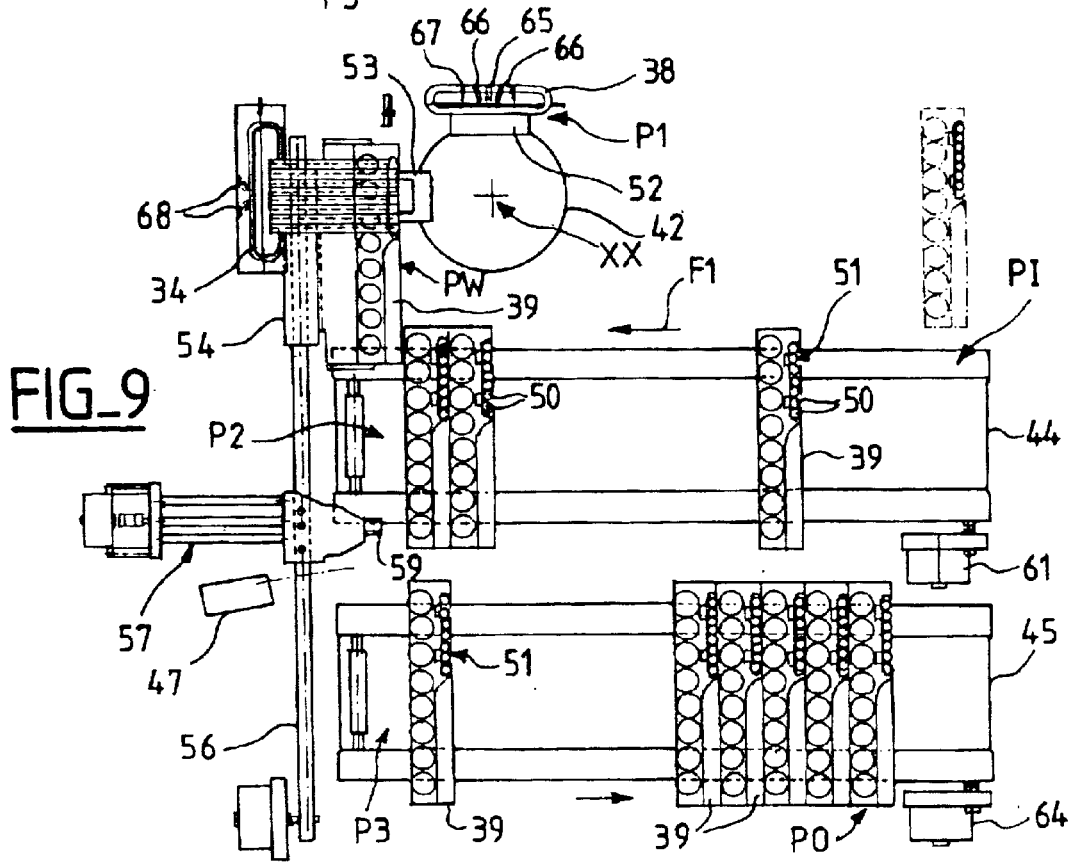

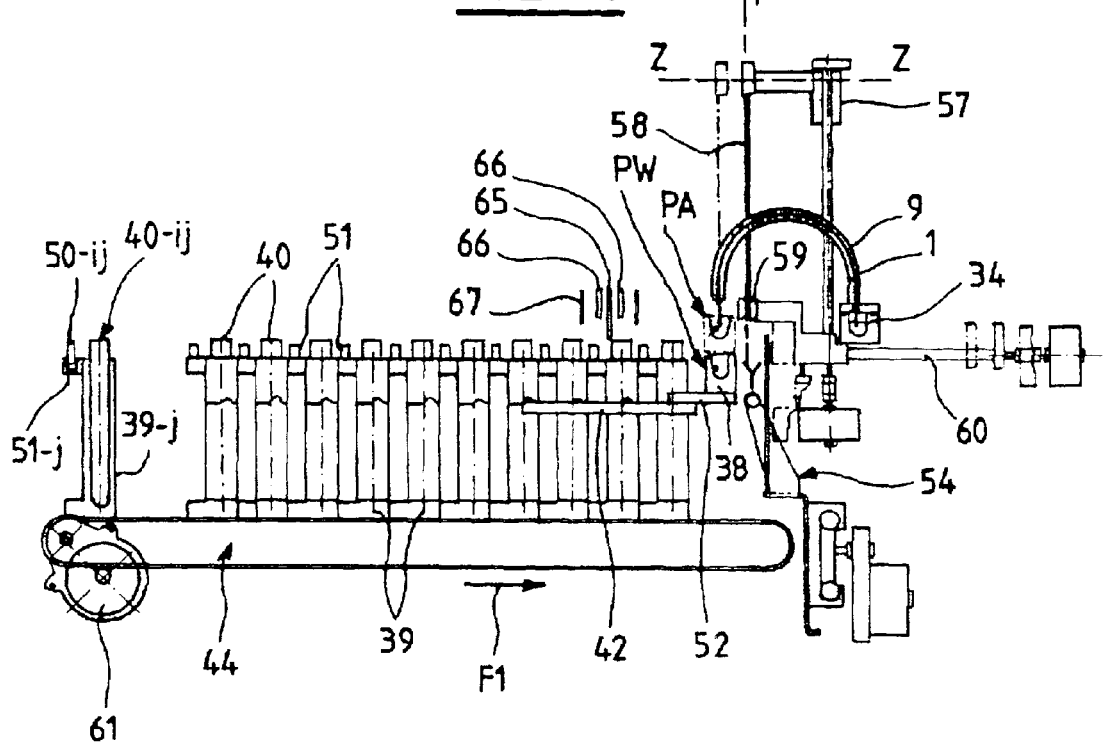
FIG_10
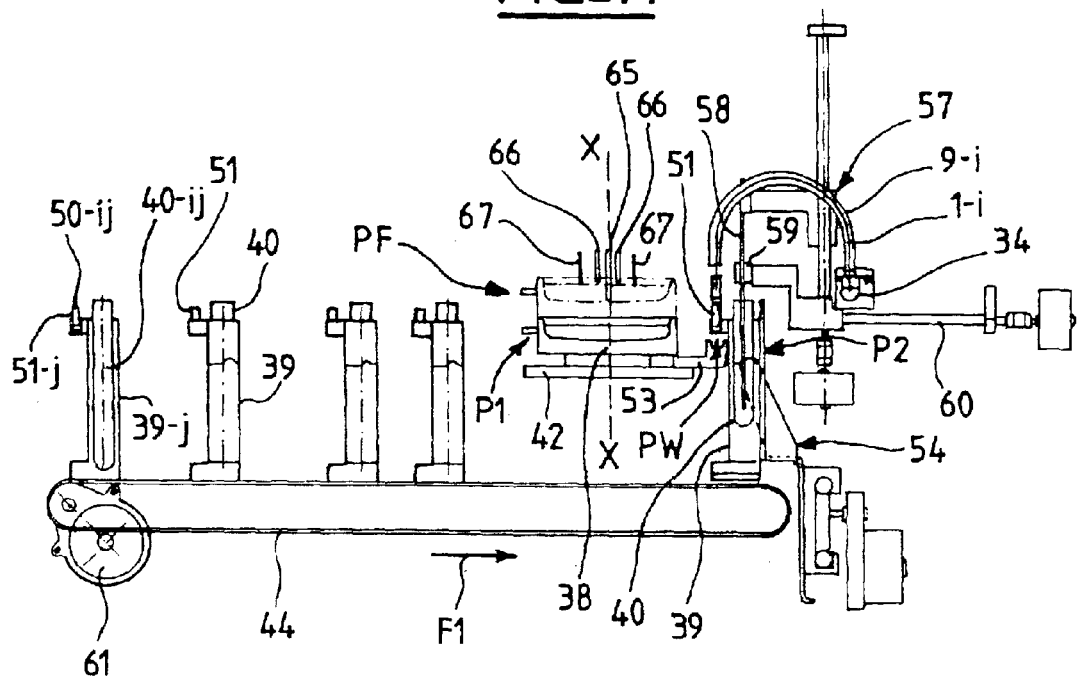
FIG_11

DEVICE FOR ANALYZING SAMPLES BY MULTI-CAPILLARY ELECTROPHORESIS WITH SOLID/SOLID TEMPERATURE REGULATION

The invention relates to the field of analyzing samples by multichannel capillary electrophoresis.

BACKGROUND OF THE INVENTION

It relates more particularly to devices comprising firstly a multiplicity of capillaries for analyzing samples in parallel, secondly receiver means for receiving at least the central portions of the capillaries remote from their ends, and thirdly regulator means co-operating with the receiver means to regulate the temperature of the capillaries.

A device of this type is described in particular in U.S. Pat. No. 5,045,172. The capillaries of that device are used in a hollow case within which a cooling fluid circulates for temperature regulation purposes.

That method of temperature regulation requires a complex hydraulic circuit comprising at least a pump, a fluid reservoir, sealing means, means for regulating the fluid flow rate, and possibly also a heat exchanger.

Such a circuit increases the size of the device, requires regular maintenance, and disturbs the capillaries because of the turbulence that exists inside the case.

Furthermore, that type of regulation by means of a fluid is unsatisfactory in terms of reproducibility between capillaries.

Also, it is difficult to replace a faulty capillary because all of the capillaries are housed in the same case.

Finally, that type of device requires a large amount of manipulation, in particular of the samples to be analyzed, thereby making it impossible to perform analyses at a rate sufficient for use in a clinical chemical laboratory.

Other solutions have been proposed, for example in document U.S. Pat. No. 5,413,686, however they do not provide entire satisfaction.

OBJECTS AND SUMMARY OF THE INVENTION

An object of the invention is thus to resolve the above-mentioned drawbacks in full or in part.

To this end, the invention provides a device of the type described in the introduction in which, firstly, the capillary receiver means comprise a multiplicity of independent units closely enclosing the central portions of the capillaries and made of a material that is thermally conductive and electrically insulating, and secondly the temperature regulation means are arranged to provide heat exchange with the units via a solid/solid exchange in such a manner as to regulate the temperature of the capillaries via said units.

The term "closely enclosing" is used herein to mean that the material of the unit is in surface contact with the outside surface of a capillary. The term "solid/solid exchange" is used to mean that heat exchange takes place by transfer from one solid surface to another solid surface, and not from a solid surface to a liquid or gaseous surface.

This provides very effective temperature regulation and enables any faulty capillary to be replaced independently of the others.

In an advantageous embodiment, first link means are provided formed of thermally conductive walls that define housings for closely receiving the units. Still more preferably, the first link means are constituted by a multiplicity of independent second link means comprising at least three walls that are substantially mutually perpendicular and leaving an opening for housing a unit, each second link means co-operating with its unit to constitute an independent cartridge.

The unit can be made of resin, e.g. of the Stycast type (trademark registered by National Search and Chemical Company). It can be flexible or rigid. It can be shaped prior to being introduced into the housing formed by the first link means, or it can be injected directly into the housing. The unit can be extractable or not, depending on how it is made.

According to another characteristic of the invention, detector means are provided capable of supplying information about the samples traveling in a selected zone of each capillary.

Preferably, these detector means comprise a source delivering light radiation at a selected wavelength, a light radiation detector, a multiplicity of first optical fibers each having a first end receiving the light radiation and a second end delivering the light radiation to the selected zone of a capillary, and a multiplicity of second optical fibers each comprising a first end picking up the light radiation from the associated first optical fiber after it has interacted with the sample components traveling through the selected zone of the capillary, and a second end delivering said light radiation that has interacted to the detector.

Such a detector can advantageously be implemented in the form of a charge-coupled device (CCD) having a multiplicity of detector elements each coupled to the second end of a corresponding second optical fiber. The term "element" is used herein to mean one or more detection pixels. Detection is performed using a single detector simultaneously on the various capillaries such that the response coefficient of the detector is substantially constant regardless of which capillary is involved, thereby making it possible for the reproducibility of analysis to be improved considerably from one capillary to another.

Preferably, in the selected zone, each capillary has an internal cross-section of area that is greater than in its other portions. This can be achieved either by coupling together capillaries of different dimensions, or else by using "bubble" capillaries of the type described in U.S. Pat. No. 5,061,361 and sold by Agilent Technologies. As a result, the path followed by the light through the capillary is lengthened, thus considerably increasing the sensitivity of detection.

According to yet another characteristic of the invention, first and second reservoirs are provided each fitted with a single first or second electrode and capable of receiving the first or the second ends respectively of the capillaries together with high voltage power supply means enabling a selected potential difference to be established between the first and second electrodes. All of the first ends of the capillaries are thus placed at substantially the same depth in the analysis fluid, and the electric field is distributed in uniform and substantially symmetrical manner over the ends, thereby further improving the reproducibility of analyses.

Preferably, means are provided that are capable of establishing a selected pressure difference between the first and second reservoirs that is either positive or negative, such that fluid flow can take place from the first reservoir to the second reservoir and vice versa (which fluid is generally a liquid, but could be a gas, e.g. to unplug a capillary). This enables the capillaries to be cleaned under pressure, preferably using a counterflow, and consequently enables the time required for cleaning the capillaries to be reduced considerably, while also improving the quality of such cleaning.

The invention also provides a method of analyzing samples by capillary electrophoresis, the method comprising at least the following steps:

introducing samples into a multiplicity of capillaries each having a central portion closely incorporated in an independent unit made of a material that is thermally conductive and electrically insulating;

applying a selected potential difference between the opposite ends of the capillaries in order to separate the components of the samples, while regulating the temperature of the capillaries by heat exchange via a solid/solid exchange between said units and regulator means, preferably of the Peltier type; and detecting the components in a selected zone of the capillaries.

BRIEF DESCRIPTION OF THE DRAWINGS

Other characteristics and advantages of the invention will appear on examining the following detailed description and the accompanying drawings, in which:

FIG. 1 is an exploded view of a portion of a capillary cartridge of the invention;

FIG. 2 is a perspective view of a complete cartridge;

FIG. 3 is a perspective view of a block of cartridges prior to installation in a device of the invention;

FIG. 4 is a cross-section view of the FIG. 3 cartridge block after installation in a device of the invention;

FIG. 5 is a cross-section view of the portion of the device of the invention that provides coupling between a capillary and the detector means;

FIGS. 6A and 6B are diagrams showing respectively the coupling between the first detection optical fibers and the light source, and the coupling between the second detection optical fibers and the sensor;

FIG. 7 is a diagrammatic detail view showing the coupling between a second optical fiber and a detector element of the sensor;

FIG. 8 is a plan view showing a portion of the device of the invention, while analyzing samples;

FIG. 9 is a plan view of the FIG. 8 device while samples are being introduced into the capillaries;

FIG. 10 is a side view of a portion of the device of the invention during transfer of the upstream reservoir from the rest, first position, to the analysis position, and;

FIG. 11 is a side view showing the same portion of the device as FIG. 10, specifically while transferring samples from a tube to a cup, and while cleaning/filling the upstream reservoir.

MORE DETAILED DESCRIPTION

The accompanying drawings are essentially of certain character. Consequently, they can serve not only to complement the invention, but also to contribute in defining it, where appropriate.

The invention relates to a device for analyzing (or processing) samples by multi-capillary electrophoresis. The term "multi-capillary" is used herein to mean that at least two capillaries are placed in parallel for analyzing at least two samples substantially simultaneously. By way of example, the description relates to an electrophoresis device capable of analyzing eight samples simultaneously by means of eight capillaries. Naturally, the invention is not limited to this particular embodiment.

Capillary electrophoresis is a technique that is well known to the person skilled in the art. It consists in causing the various molecules making up a sample that is to be analyzed to migrate inside a capillary which contains, for example, a suitable buffer solution. For this purpose, capillary 1-i (in this example i=1 to 8) has two opposite ends 2 and 3 which are placed in liquid media (buffer solution) which are taken to different electric potentials after the sample has been introduced into the first end 2. The electric potential differences (or voltages) can lie in the range about a few tens of volts to a few hundred thousand volts, and more preferably can lie in the range about 2000 volts to 30,000 volts.

Under the effect of the resulting electric field, the molecules of the sample that have previously been introduced via the first end 2 (i.e. the upstream end) of capillary 1-i migrate inside said capillary 1 at different speeds in particular as a function of their respective charge/mass ratios, as a function of the nature of the buffer solution used (pH, conductivity, etc.), and as a function of the value of the electric field. On coming close to the second end 3 (i.e. the downstream end), the various molecules as separated in this way are analyzed (or detected) in a selected zone 4 by detector means which are described below.

Unfortunately, the electric field also causes the capillary to be heated by the Joule effect. Temperatures of 70° C. can thus be reached in the capillaries and this affects in particular the stability of the sample, the viscosity of the buffer solution used, chemical equilibria, pH, and the respective migration times of the various molecules of the sample.

To remedy this drawback, the invention proposes an analysis device in which each capillary 1-i is temperature regulated by exchanging heat over a solid/solid exchange, and preferably by the Peltier effect.

For this purpose, receiver means are provided comprising at least mutually independent units 5-i made of a material that is thermally conductive and electrically insulating. Each unit 5-i closely encloses the central portion 7 of the corresponding capillary 1-i, i.e. covers it in such a manner as to make surface ("solid") contact with said central portion of the capillary. Only the detector portion 4 and the upstream and downstream ends 2 and 3 of the capillary 1-i are free, i.e. not included or integrated within the unit 5-i.

The receiver means preferably also include link means 6-i constituted by thermally conductive walls 8 defining respective housings 63 (in this case eight housings), each serving to receive a respective unit 5-i closely (as defined above). Surface ("solid") contact is thus established between the walls 8 constituting the link means 6 and the units 5-i which include the capillaries 1-i.

In the example shown in FIGS. 1 to 4, the link means 6 and the units 5-i which include the various capillaries 1-i constitute a multiplicity (in this case equal to eight) of mutually independent cartridges 9-i. More precisely, each cartridge 9-i is preferably constituted by one unit 5-i and three walls 8, which walls are substantial perpendicular to one another so as to leave an opening 63 for receiving the unit.

When the receiver means comprise only units 5-i, each unit, together with the capillary it contains, constitutes a cartridge.

The units 5-i are preferably made of a resin material that is either flexible or rigid. By way of example, it can be a material of the Stycast (trademark registered by National Search and Chemical Company), which provides high thermal conductivity. However other thermally conductive materials could be envisaged.

The unit 5-i can be made prior to being installed within the walls 8 which in the example shown constitute the link means 6.

However, as shown in FIGS. 1 to 3, the unit 5-i can also be formed directly inside the link means 6-i, e.g. by injecting material, and after the capillary 1-i has been put into position. Under such circumstances, in order to ensure that the capillary 1-i can be embedded (or totally integrated) in the unit 5-i, it is advantageous for the capillary to carry spacers 10 having substantially the same dimensions as the housing 63 defined between the walls 8. Thus, once the capillary has been installed inside the housing 63, it only remains to inject the resin so as to make the unit 5.

The cartridges are preferably curved in shape so as to reduce overall size and so as to enable the ends of the capillaries to be positioned substantially vertically.

Each upstream and downstream end 2 and 3 of a capillary 1 is preferably provided with an endpiece 11 enabling it to be secured relative to a support plate 62 (see FIG. 4). Naturally, the endpieces placed at the opposite ends 2 and 3 could be different.

Also preferably, the inside of each capillary 1 along which the fluids and samples travel, has a selected detection zone 4 in which it presents a cross-section of greater area (see FIG. 5) than in its portions outside said zone. For example, when the capillary is in the form of a circular cylinder, the inside diameter of its more open portion in the selected zone 4 is greater than its inside diameter in its other portions 2, 3, and 7. Advantageously, this makes it possible to increase the optical pathlength of the light radiation used by the detector means to analyze the separated molecules in the selected zone 4. Naturally, it is also possible to use capillaries of inside diameter that is constant, even in the detection zone 4.

The inside diameter of the capillaries lies in the range about 1 $\mu$m to about 20 $\mu$m, and preferably in the range about 20 $\mu$m to about 100 $\mu$m. Even more preferably, it is equal to about 25 $\mu$m.

To confer a certain amount of flexibility to the capillaries 1-i without causing them to break, they are conventionally covered in a polyimide coating. This material absorbs light radiation so it must be removed from the selected detection zone.

In addition, it is particularly advantageous for each capillary to be provided in the selected zone 4 with a coupling endpiece 12 enabling a portion of the detector means to be secured on either side of the selected zone 4, e.g. the ends of optical fibers along which the light radiation travels.

The coupling endpiece 12 is preferably implemented in the form of a machined or molded block in which a first through housing 13 is formed for receiving both the downstream end 3 and the selected zone 4 of the capillary 1, and in which second and third housings 14 and 15 are formed substantially perpendicularly to the first housing 13 and opening out into it, serving to receive respective endpieces 16 placed on the ends of the upstream and downstream fibers 26 and 29 of the detector means.

In the embodiment shown in FIGS. 1 to 5, the second and third housings 14 and 15 communicate with the first housing 13 at the selected zone 4 and they are placed substantially facing each other. The dimensions of these second and third housings 14 and 15 formed in the coupling blocks 12 correspond to those of the end portions 19 of the endpieces 16. In addition, the portion of the first housing 13 through which the downstream end 3 of the capillary 1 extends is of dimensions that match those of the end portion 20 of the endpiece 11. The embodiment of the coupling block 12 shown in FIG. 5 is a variant of the embodiment shown in FIG. 1.

Preferably, the walls 8 of each cartridge 9-i define a housing 21 at the end through which the downstream end 3 of the capillary 1-i extends, which housing serves to secure at least a portion of the coupling block 12 relative to the cartridge as a whole. This housing 21 communicates with the outside via openings 22 designed to pass the endpieces 16.

Naturally, when the cartridge is constituted solely by a unit 5 together with its capillary 1, the coupling block 12 is engaged on the end of the unit 5.

The various cartridges 9-i (in this case i=1 to 8) fitted with respective coupling blocks 12 are preferably secured side by side on the support 62. The endpieces 16 for the ends of the optical fibers 26 and 29 are then inserted into the second and third housings 14 and 15 of the coupling blocks 12.

Also preferably, and as shown in FIG. 4, a thermally conductive cover 23, e.g. made of aluminum or of alumina is provided over the cartridges 9-i and in surface contact therewith. This cover 23 serves to hold two modules (or units) 24 (preferably Peltier modules) and to distribute thermal contact between the Peltier modules 24 and the walls 8 in uniform manner. It serves as a kind of thermal interface.

Naturally, the Peltier modules could be held by auxiliary support means in contact with the walls 8, but installing them in the cover 23 makes it easier to take action on the cartridges 9 when one of them is faulty. Under such circumstances, it suffices to remove the cover 23 so as to gain access directly to the cartridges 9, and then to replace one of them without acting on the others.

Reference is now made more particularly to FIGS. 6A and 6B while describing a preferred embodiment of the detector means of a device of the invention.

As known to the person skilled in the art, numerous optical analysis methods can be considered for detecting and/or analyzing the various molecules separated in the capillaries 1.

Preferably, the detector means of the device of the invention comprise a monochromatic source constituted by a lamp delivering a continuous spectrum and by a monochromatic filter for selecting a single selected wavelength. By way of example, it is possible to use a deuterium lamp that delivers a continuous spectrum between about 180 nm and about 390 nm, together with an interference filter selecting light radiation having a wavelength of about 200 nm.

This light radiation is brought to the selected zones 4-i by upstream optical fibers 26-i. The first ends 27 of these upstream optical fibers 26-i are connected to a unit 25 containing the lamp and the monochromatic filter, while the second ends 28 thereof, opposite from the first ends 27, are provided with respective coupling endpieces 16 whose end portions 19 are for insertion into the second housings 14 of respective coupling blocks 12-i.

Similarly, to collect the light radiation that has come from the upstream optical fibers 26-i and that has interacted with the molecules traveling inside the capillaries 1-i in the selected zones 4-i, downstream optical fibers 29-i are provided. The first ends 30 of the downstream optical fibers 29-i are provided with respective coupling endpieces 16 whose end portions 19 are for insertion into third housings 15 of respective coupling blocks 12. The second ends 31 of the downstream optical fibers 29-i opposite from their first ends 30 are connected to a detector module 32.

The detector module 32 is preferably a charge-coupled device (CCD) having at least as many detector elements 48 as there are downstream optical fibers 29 (in this case eight). As shown in FIG. 7, a detector element 48-i can comprise one or more detector pixels 49 (in the example shown, each element comprises ten pixels). The number of pixels 49 associated with an element 48-i depends on the numerical aperture of the second end 31 of the downstream optical fiber 29-i and on the distance between said end and the pixels. As a result, it is possible with a single detector to perform detection simultaneously on all of the capillaries 1-i, thereby ensuring response coefficients that are substantially constant from one capillary to another and consequently improving the reproducibility of measurements (or analyses).

Also preferably, the diameter of the inner portion 17 of the upstream optical fibers 26 is selected to be considerably smaller than that of the inner portions 18 of the downstream optical fibers 29. The particular diameters selected depends on the desired optical resolution and on the desired energy transmission between the upstream and downstream optical fibers 26 and 29.

For example, it is possible to use silica/silica type optical fibers. Furthermore, the CCD detector 32 could be of the kind sold by Hamamatsu under the reference S5462-256Q.

This CCD detector 32 is connected via an interface 33 to a control module (not shown in the figures) for the device of the invention, so as to deliver signals thereto that are representative of the information picked up in the capillaries.

Advantageously, an additional optical fiber is provided between the source and the CCD detector in order to measure variations in the energy from the lamp so as to be able to correct the analysis data. The CCD detector 32 consequently has an additional detector element 48.

Other analysis techniques could be used in the device of the invention. For example, it is also possible to perform detection by laser induced fluorescence or by electrochemical detection.

As shown more clearly in FIGS. 4 and 5, the downstream ends 3 of the capillaries 1 are designed to be received in a downstream reservoir 34 which contains a liquid (buffer solution) placed to a first electric potential selected by means of a single electrode 35 coupled to a high voltage electrical power source (not shown) controlled by the control module.

The coupling blocks 12 and the downstream reservoir 34 are preferably arranged so that they can be secured to one another in releasable manner. More particularly, it is highly advantageous for them to be secured to one another in an impervious manner so that the liquid in the downstream reservoir 34 can be pressurized by means of a pressurization circuit 36 (shown in part in FIG. 4). Thus, by establishing pressure in the downstream reservoir 34 that is different from the pressure that exists at the upstream ends 2 of the capillaries 1-i (placed in cups 50-i or in an upstream reservoir 38), it is possible to cause a liquid to travel under pressure either from the downstream reservoir 34 towards the upstream reservoir 38 by applying positive pressure, or from the upstream reservoir 38 towards the downstream reservoir 34 by applying negative pressure (suction). This makes it possible to wash (or rinse) the capillaries after and/or before analysis both quickly and effectively, or indeed to fill them with a buffer solution prior to introducing samples, and also to inject samples.

To enable the liquid required for performing analyses or for washing to be introduced into the downstream reservoir 34 (e.g. a buffer solution or a rinsing solution of the NaOH type at a concentration lying in the range about 0.1 M to 1 M), the downstream reservoir advantageously includes a duct 37 that is fed from a liquid feed module (not shown) controlled by the control module.

Reference is made below more particularly to FIGS. 8 to 11 for describing an embodiment of the device of the invention in detail.

The samples are initially placed in test-tubes 40-ij housed in racks 39-j (in this example i=1 to 8 and j=1 to N). Each rack 39-j also has a strip 51-j carrying cups 50-ij, with the number of cups preferably being equal to the number of test-tubes 40-ij. These cups 50 are to receive the samples, possibly after dilution, as described below, and to deliver the optionally diluted samples to the upstream ends 2 of the capillaries 1-i.

The ends 2 of the capillaries are secured in an analysis position PA. It is therefore necessary to move the upstream reservoir 38 and the strip 51 in turns into the analysis position PA in order to be able to perform analyses.

For this purpose, the device has displacement means 42 that are capable firstly of moving the upstream reservoir 38 between a first rest position P1 (see its location in FIGS. 9 and 11) and a waiting position PW (see location in FIGS. 9–11), preferably located substantially beneath the analysis position PA, and then from said waiting position PW to the analysis position PA, and secondly to move the strip 51-j from the waiting position PW to the analysis position PA.

Preferably, the displacement means comprise a carousel 42 capable of being rotated about an axis XX and of being displaced vertically along said axis XX. More precisely, and as is shown more clearly in FIGS. 8 to 11, the carousel 42 has two brackets 52 and 53 projecting radially at substantially 90° from each other. Rotating the carousel 42 through one-fourth of a turn makes it possible for one of the brackets 52 to move the upstream reservoir 38 from its rest position P1 to the waiting position PW. Moving the carousel 42 axially (see FIGS. 10 and 11) makes it possible to move the upstream reservoir 38 or the strip 51-j from the waiting position PW to the analysis position PA, or vice versa, using one or other of the brackets 52–53.

In the analysis position PA (shown by dashed lines in FIGS. 10 and 11), the upstream ends 2 of the capillaries 1-i are thus received in the upstream reservoir 38.

Furthermore, the displacement means preferably include transfer means 54 suitable for moving the rack on which the strip 51-j is installed between the waiting position PW and a second rest position P2. Advantageously, this transfer means is a carriage 54 mounted to slide on a rail 56.

In this second rest position P2, samples are pipetted and diluted. The device consequently has a pipette/dilution module 57 (shown in part in FIGS. 10 and 11) having a hollow needle 58 capable of being moved in translation along a substantially vertical axis YY to suck up the sample placed in one of the test-tubes 40-i via a first end and then diluted with a diluant which preferably arrives via a second end of the needle which is fed by one or more ducts 60 connected to one or more reservoirs. The volume of diluant is controlled by the control module of the device and it is selected as a function of the type of sample to be analyzed. Once dilution has been performed, the needle 58 places the diluted sample in the associated cup 50-i, by moving the needle 58 in translation along a substantially horizontal axis ZZ (see FIG. 10) coupled with moving the carriage 54 in translation perpendicularly to said axis ZZ. All of these displacements are controlled by the control module which is programmed for this purpose.

In addition, in order to enable a multiplicity of racks 39-j to be treated sequentially, the device of the invention preferably has supply means which advantageously include a first conveyor belt 44 driven by a motor 61 under the control of the control module and on which a plurality of preferably linear type racks 39-j can be placed. The racks are introduced one after another at an upstream end of the first conveyor belt, thereby defining an introduction position PI, such that they are advantageously placed perpendicularly to their travel direction (represented by arrow F1), one behind another. The first belt 44 thus conveys them one after another from the introduction position PI towards the second rest position P2 (e.g. defined by the downstream end of the conveyor belt 44) from which they can be taken by the carriage 54.

In addition, the device also preferably includes means for removing racks after the samples have been analyzed. Advantageously, these removal means comprise a second conveyor belt 45 likewise driven by a motor 64 (possibly the same motor as drives the first conveyor belt 44), and preferably placed in parallel with the first conveyor belt 44. This second conveyor belt 45 has an upstream first end which, for example, defines a third rest position P3 for the racks 39 coming from the analysis position PA, and a downstream second end remote from its first end and defining a rack extraction position PO. It is the carriage 54 which takes a rack 39 after its samples have been analyzed from the waiting position PW to the third rest position P3 so that it is removed by the second conveyor belt 45.

As a result, the first conveyor belt 44 serves to introduce the racks 39 with their samples to be analyzed into the device while the second conveyor belt 45 serves to recover the racks after their samples have been analyzed and to move them out from the device. The device can be fed with racks on a continuous basis insofar as each time a rack is removed by the second belt a position becomes free on the first belt for receiving a new rack with samples to be analyzed.

Like the downstream reservoir 34, the upstream reservoir 38 has a single electrode 46 connected to the high voltage power supply module. This module can thus operate under the control of the control module of the device to establish a potential difference between the two electrodes 35 and 46. This difference can be matched to requirements. The upstream electrode 46 is preferably placed at a positive electrical potential while the downstream electrode 35 is at ground potential, but numerous other combinations could be envisaged.

Advantageously, the device of the invention also has a plurality of liquid feed circuits (buffer solution and rinsing and washing solutions) which circuits open out substantially in the vicinity of the first rest position P1 and at the duct 37 of the downstream reservoir 34.

As shown more clearly in FIG. 10, the feed circuit of the upstream reservoir 38 includes a subcircuit connected to a duct 65 for extracting buffer solution, and at least one subcircuit connected to another duct 66 for supplying rinsing or washing liquid and buffer liquid (in the example shown, two rinsing subcircuits are provided). Furthermore, liquid level detectors 67 and 6B can be provided in each reservoir. The upstream reservoir 38 is fed with buffer liquid or with rinsing liquid preferably after the carousel 42 has moved vertically along the axis XX (see FIG. 11 where the feed position PF is represented by chain-dotted lines).

The device of the invention preferably also includes a bar code detector module 47 for enabling the control module to make sure that the testtube-carrying rack that is being presented has not already been analyzed. This detector module can also read bar codes placed on each test-tube 40-i so that each sample can be associated with an electrophoregram. Thus, by supplying a sample identifier to the control module it is possible to gain immediate access to its electrophoregram as stored in a memory.

The rack detector module 47 is preferably located substantially facing the second rest position P2.

A sample analysis cycle is described below with reference to a rack 39-j which has already reached the second rest position P2.

In a first step, the carriage 54 takes hold of the rack to place it beneath the pipette/dilution module 57, after which the module extracts the sample placed in the first tube 40-ij, dilutes it, and puts the diluted sample in cup 50-ij. It then reproduces the same operations on each of the other samples. At the same time, the eight samples of the preceding rack 39-(j-1) are being analyzed by the capillaries 1-i. This step of diluting samples (n) takes place during the step of analyzing samples (n-1).

In a second step, once the analysis of the preceding rack has been finished, the downstream reservoir 34 is emptied while the upstream reservoir 38 remains in the analysis position PA. The downstream reservoir 34 is then filled with a washing solution (NaOH, for example) and then a positive pressure difference is established between the downstream reservoir 34 and the upstream reservoir 38 for a determined length of time. The downstream reservoir 34 is then emptied again and preferably rinsed prior to being filled with a buffer solution. Thereafter a positive pressure difference is established between the downstream reservoir 34 and the upstream reservoir 38 for a selected duration.

In a third step, the upstream reservoir 38 is lowered together with the carousel 42 from the analysis position PA towards the waiting position PW, and then the carousel 42 is rotated to place the upstream reservoir 38 in the first rest position P1.

In a fourth step, the rack 39-j is moved from the second rest position P2 to the waiting position PW and then the strip 51-j is separated from the rack 39-j by one of the brackets 53. The strip 51-j is then raised together with the carousel 42 from the waiting position PW to the analysis position PA.

In a fifth step, a negative pressure difference is established between the downstream and upstream reservoirs 34 and 38 for a selected duration so that the samples penetrate a short distance into the capillaries 1-i. Thereafter the strip 51-j is lowered from the analysis position PA to the waiting position PW where the rack 39-j is waiting for it, and they are reconnected. The carriage 54 then moves the rack 39-j in translation from the waiting position PW to the third position P3 where it is taken over by the second conveyor belt 45 to be removed. Thereafter, the carriage 54 comes to take rack 39-(j+1) from the second rest position P2. Substantially simultaneously, the upstream reservoir 38 is raised from its feed position PF so as to be emptied and then rinsed, and finally filled with a buffer solution.

In a sixth step, the upstream reservoir 38 is lowered to the first rest position P1 and the carousel 42 is turned to place the upstream reservoir 38 level with the waiting position PW. The upstream reservoir 38 is then raised by moving the carousel 42 in translation until the upstream reservoir 38 is placed in the analysis position PA.

In a seventh step, a selected potential difference is established between the upstream and downstream electrodes 46 and 35 in order to perform analysis on the samples of rack 39-j. The light rays traveling inside the working portions 17 of the upstream optical fibers 26 pass through the selected zones 4 of the capillaries 1-i and interact with the sample molecules that travel under the effect of the electric field induced by the potential difference, after which said light rays are picked up by the working portions 18 of the downstream optical fibers 29-i. They then reach the pixels of the detector CCD elements 32 where they are converted into electrical signals and transmitted via the interface 33 to the control module. These signals are then used by the control module to produce an electrophoregram for each sample, which electrophoregram is displayed, preferably in real time, on a monitor. Thereafter the analysis data is stored for subsequent processing. Simultaneously, the first step is applied to rack 39-(j+1).

Once the first step has been completed, steps 2 to 7 are repeated to analyze the diluted samples which have just been placed in the cups 50-i(j+1) of the strip 51-(j+1) of the rack 39-(j+1).

The device of the invention can be used for capillary analysis of numerous samples. However it is particularly intended for analyzing samples of a biological nature, for example and in non-limiting manner samples such as blood, serum, plasma, urine, cerebrospinal fluid, saliva, and tears.

The device of the invention presents numerous advantages, and in particular:

it provides particularly effective solid/solid type temperature regulation;

it considerably simplifies the electrical installation because the upstream and downstream reservoirs have a single electrode each. In addition, these single electrodes guarantee uniform distribution of the electric field in the reservoirs, thereby improving reproducibility from one capillary to another;

it simplifies and improves the detection of the molecules in various samples and the reproducibility of such detection, because its has a common detector for the various capillaries;

it provides washing that is of good quality and fast because said washing is performed under pressure;

it enables analyses to be performed at high throughput, because the various steps of dilution, analysis, and washing are automated and because of the way in which it is fed with racks (preferably continuously); and it is easy to use and maintain because there is no human intervention on the samples, and any one capillary can be replaced without it being necessary to take action on the other capillaries.

The invention is not limited to the embodiment of the device and the implementation of the method described above purely by way of example, and it covers any variant that the person skilled in the art could envisage within the ambit of the claims below.

Thus, the above description relates to a device fitted with means for feeding it with a multiplicity of racks, and means for removing those racks. However, the device need not have such means, in which case the racks would be put into place and removed manually at the second rest position.

The description above relates to a device in which the samples are diluted automatically. However samples could be supplied to the device in ready-diluted form, or the device could be presented with samples that do not need diluting, so it is possible to omit the pipette/dilution module. Under such circumstances, it is clear that it would be possible to omit racks and test-tubes, since a strip of cups would then be sufficient.

The description above relates to a sample being analyzed by using a buffer solution that is liquid. However the buffer solution could be viscous or semiviscous.

What is claimed is:

1. A device for analyzing samples by electrophoresis, comprising:

a plurality of capillaries each having opposite first and second ends, each being housed in an individual cartridge suitable for receiving a central portion of said capillary and spaced apart from said first and second ends thereof, each cartridge including a housing of thermoconductive, electrically insulating material, said cartridges being independently removable from said device;

a first reservoir provided with a first electrode, and a second reservoir provided with a second electrode, said first and second reservoirs being suitable for receiving the first and second ends of the capillaries, respectively;

a high voltage power supply suitable for establishing a selected potential difference between the first and second electrodes;

at least one support adapted for carrying each of said cartridges; and at least one thermoelectric Peltier unit suitable for regulating the temperature of said plurality of cartridges, the said Peltier unit being in surface contact with said cartridges so as to facilitate solid/solid heat exchange.

2. A device according to claim 1, further comprising coupling means comprising a multiplicity of first housings each suitable for receiving said selected zone of a capillary in order to hold it at a selected location, and a multiplicity of second and third housings formed substantially perpendicularly to said first housings and opening out therein at the said location, each second housing being arranged to receive the second end of a first optical fiber, and each third housing being arranged to receive the first end of a second optical fiber.

3. A device according to claim 2, wherein said second ends of the first optical fibers and said first ends of the second optical fibers are provided with respective endpieces for coupling to the second and third housings respectively of the coupling means.

4. A device according to claim 2, wherein said coupling means comprise a multiplicity of coupling element each suitable for coupling one capillary to a first optical fiber and to a second optical fiber.

5. The device according to claim 4, wherein each coupling element is received into an end of a said cartridge.

6. A device according to claim 1, further comprising means suitable for establishing a selected positive or negative pressure difference between said first and second reservoirs, said pressure difference being selected in such a manner as to establish flow from the first reservoir towards the second reservoir or from the second reservoir towards the first reservoir.

7. A device according to claim 1, further comprising displacement means arranged to move said first reservoir between a rest first position and an analysis position in which said first ends of the capillaries are received inside the first reservoir.

8. A device according to claim 7, further comprising support means for supporting a multiplicity of cups to move, said support means arranged via said displacement means, each cup being suitable for receiving a sample to be analyzed, and being movable between a waiting position and said analysis position in which each first end of a capillary is received inside a cup in order to introduce the sample it contains into said capillary.

9. A device according to claim 8, wherein the analysis position is situated substantially above the waiting position, and wherein said displacement means comprise a carousel suitable for being driven firstly in rotation between a first rest position and the waiting position, and secondly in axial translation between the analysis position and the waiting position.

10. A device according to claim 8, further comprising transfer means suitable for moving said cup support means between said waiting position and a second rest position.

11. A device according to claim 10, further comprising including supply means suitable for moving a plurality of cup support means sequentially between an introduction position and said second rest position.

12. A device according to claim 11, further comprising removal means, said removal means comprising a second conveyor belt driven by a motor and suitable for moving between the third rest position and the removal position, and wherein said supply means comprise a first conveyor belt driven by a motor and suitable for moving between the introduction position and the second rest position.

13. A device according to claim 12, wherein said supply means and said removal means are arranged to receive at least two cup support means.

14. A device according to claim 10, further comprising removal means suitable for moving a plurality of cup support means sequentially between a third rest position and a removal position, and wherein said transfer means are arranged to displace each cup support means between said second rest position and said third rest position.

15. A device according to claim 8, wherein said support means comprises cup support means, secured to a rack containing a multiplicity of test-tubes, the number of test-tubes being equal to the number of cups, each test-tube containing a sample to be transferred into an associated cup on the same rack.

16. A device according to claim 15, further comprising pipette/dilution means arranged to operate sequentially to extract the sample contained in each test-tube while in the second rest position, and then to dilute said sample with a selected diluant, and then to place the diluted sample in the associated cup on the rack.

17. A device according to claim 1, further comprising liquid feed means suitable for feeding each reservoir with cleaning solution after each sample analysis, and to feed each reservoir with buffer solution prior to each analysis.

18. The device according to claim 1, wherein each housing of thermoconductive material comprises three perpendicular walls that form an opening for receiving a block of thermoconductive material.

19. The device according to claim 18, wherein said block of thermoconductive material is made of thermoconductive resin.

20. The device according to claim 1, wherein said first and second ends of the capillaries are provided with end pieces suitable for securing said ends to said support.

21. The device according to claim 1, further comprising pressurization means, said second end of said capillaries sealingly received in said second reservoir connected to said pressurization means.

22. The device according to claim 1, further comprising: a detector optically coupled to at least one said capillaries and arranged to supply information about samples components traveling through a selected zone of each capillary, said detector means including:
a light source suitable for delivering light radiation at a selected wavelength;
a light radiation detector;
a multiplicity of first optical fibers each having a first end suitable for receiving said light radiation and a second end suitable for delivering said light radiation to a selected zone of a capillary; and
a multiplicity of second optical fibers each having a first end suitable for picking up the light radiation from the associated first optical fiber after it has interacted with the components of the sample traveling in a capillary through said selected zone of a capillary, and a second end for delivering the light radiation that has interacted to said detector.

23. A device according to claim 22, wherein said light radiation detector is a charge-coupled device having a multiplicity of detector elements each coupled to a second end of a single second optical fiber.

24. A device according to claim 22, wherein, in said selected zone each of said capillaries comprises an internal cross-section of area greater than the area of its internal section elsewhere.

25. A device for analyzing samples by electrophoresis, comprising:
a first reservoir provided with a first electrode, and a second reservoir provided with a second electrode, said first and second reservoirs being suitable for receiving a first and a second end of a capillary, respectively;
high voltage power supply means suitable for establishing a selected potential difference between the first and second electrodes;
a plurality of cartridges each including a capillary having a first end, second end and central portion spaced apart from said ends, each cartridge including a housing of thermoconductive, electrically insulating material which can cooperate to retain said central portion of a capillary, said cartridges being individually removable and replaceable from said device;
a support adapted for carrying the plurality of cartridges which are secured side by side on said support and which are individually removable and replaceable from said device; and
a cover of thermoconductive material provided over said plurality of cartridges and carrying at least one thermoelectric Peltier unit suitable for regulating the temperature of a plurality of cartridges, the said cover being in surface contact with said cartridges.

26. A device for analyzing samples by electrophoresis, comprising:
a plurality of capillaries each have opposite first and second ends and including a detection zone in which said capillary has an internal cross-section of greater area than that found in the remaining capillary, each capillary being housed in individual cartridges suitable for receiving a central portion of said capillaries and spaced apart from said first and said second ends thereof, each cartridge including a housing of thermoconductive, electrically insulating material, said cartridges being independently removable from said device;
at least one support adapted for carrying each of said cartridges;
a detecting means disposed to detect molecules within said detection zone;
and at least on thermoelectric Peltier unit suitable for regulating the temperature of said plurality of capillaries, said Peltier unit being in surface contact with said cartridges so as to facilitate solid/solid heat exchange.

27. The device of claim 26 wherein said detection zone of said capillary is not disposed within said cartridge.

* * * * *

UNITED STATES PATENT AND TRADEMARK OFFICE
CERTIFICATE OF CORRECTION

PATENT NO. : 6,780,300 B1
DATED : August 24, 2004
INVENTOR(S) : Alberto Fei

It is certified that error appears in the above-identified patent and that said Letters Patent is hereby corrected as shown below:

Title page,
Item [75], Inventor, "Fei Alberto, Firenze (IT)" should be -- Fei, Alberto, Firenze (IT) --.

Column 4,
Lines 13 and 15, "range about" should be -- range from about --.

Column 5,
Line 26, "capillary 1 along" should be -- capillary 1, along --.
Line 40, "range about" should be -- range of about --.

Column 7,
Line 23, "depends" shoud be -- depend --.

Column 8,
Line 33, "900" should be -- 90º --.

Column 9,
Line 61, "testtube-carrying" should be -- test tube-carrying --.

Column 12,
Line 29, "coupling element each" should be -- coupling elements each --.
Line 42, "rest first position" should be -- first rest position --.

Column 13,
Line 45, "about samples compo-" should be -- about samples of compo- --.

Column 14,
Line 6, "zone each of" should be -- zone, each of --.
Line 38, "each have" should be -- each having --.

UNITED STATES PATENT AND TRADEMARK OFFICE
CERTIFICATE OF CORRECTION

PATENT NO.   : 6,780,300 B1
DATED        : August 24, 2004
INVENTOR(S)  : Alberto Fei It is certified that error appears in the above-identified patent and that said Letters Patent is hereby corrected as shown below:

Column 14 (cont'd),
Line 53, "at least on" should be -- at least one --.

Signed and Sealed this

First Day of February, 2005

JON W. DUDAS
*Director of the United States Patent and Trademark Office*